(12) United States Patent
Tsubouchi et al.

(10) Patent No.: US 6,841,713 B2
(45) Date of Patent: Jan. 11, 2005

(54) PROCESS FOR PREPARING BICYLO[2.2.1] HEPTANE DERIVATIVES

(75) Inventors: Toshiyuki Tsubouchi, Chiba (JP); Yukio Yoshida, Chiba (JP); Motohisa Ido, Chiba (JP); Masahiro Katayama, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 368 days.

(21) Appl. No.: 10/181,433

(22) PCT Filed: Feb. 6, 2001

(86) PCT No.: PCT/JP01/00811

§ 371 (c)(1),
(2), (4) Date: Jul. 25, 2002

(87) PCT Pub. No.: WO01/58838

PCT Pub. Date: Aug. 16, 2001

(65) Prior Publication Data

US 2003/0045762 A1 Mar. 6, 2003

(30) Foreign Application Priority Data

Feb. 10, 2000 (JP) ........................................ 2000-033164

(51) Int. Cl.$^7$ ................................................. C07C 5/25
(52) U.S. Cl. ........................ 585/664; 585/666; 585/667; 585/668; 585/669; 585/670; 585/317
(58) Field of Search ................................ 585/664, 666, 585/667, 668, 669, 670, 317

(56) References Cited

FOREIGN PATENT DOCUMENTS

| JP | 49-69650 | 7/1974 |
| JP | 6-40956 | 2/1994 |

*Primary Examiner*—Thuan Dinh Dang
(74) *Attorney, Agent, or Firm*—Oblon, Spivak, McClelland, Maier & Neustadt, P.C.

(57) ABSTRACT

The invention relates to economical and efficient methods for producing 2-methylene-3-methylbicyclo[2,2,1]heptane, 2,3-dimethylbicyclo[2.2.1]hept-2-ene and the like that are useful for materials of producing base oil of traction drive fluid for traction drive lubricating oil. The methods comprise reacting one or more $C_{3-4}$ acyclic olefins with cyclopentadiene and isomerizing the resulting bicyclo[2.2.1]heptene derivatives in the presence of an isomerization catalyst to give one or more bicyclo[2.2.1]heptane derivatives.

13 Claims, No Drawings

PROCESS FOR PREPARING BICYLO[2.2.1] HEPTANE DERIVATIVES

TECHNICAL FIELD

The present invention relates to novel methods for producing bicyclo[2.2.1]heptane derivatives. More precisely, the invention relates to economical and efficient methods for producing 2-methylene-3-methylbicyclo[2.2.1]heptane, 2,3-dimethylbicyclo[2.2.1]hept-2-ene, 2-ethylidenebicyclo[2.2.1]heptane and 2-ethylbicyclo[2.2.1]-hept-2-ene that are useful for materials of producing a base oil of traction drive fluid used for a lubricating oil for driving a fraction drive apparatus.

BACKGROUND ART

Traction drive fluid that is used for traction drive lubricating oil for driving a traction drive apparatus for stepless regulators in automobiles and industrial machines is required to have specific properties of high traction coefficient and low pour point. To meet the requirement, cyclic compound derivatives are used in base oil of traction drive fluid. For example, dimers of bicyclo[2.2.1]heptane derivatives have been proposed (Japanese Patent No. 2,060,214).

Therefore, bicyclo[2.2.1]heptane derivatives, especially 2-methylene-3-methylbicyclo[2.2.1]heptane, 2,3-dimethylbicyclo[2.2.1]hept-2-ene, 2-ethylidenebicyclo[2.2.1]heptane and 2-ethylbicyclo[2.2.1]-hept-2-ene are important compounds as materials for producing base oil of traction drive fluid.

Heretofore, the compounds of the type are obtained, for example, by reacting crotonaldehyde with dicyclopentadiene through Diels-Alder reaction, then hydrogenating the reaction product and dehydrating it. The process of producing bicyclo[2.2.1] compounds requires three steps of Diels-Alder reaction, hydrogenation and dehydration. Another problem with the process is that the reactant crotonaldehyde is relatively expensive and therefore the production costs are high.

Accordingly, it is desired to develop more economical and efficient novel methods of producing bicyclo[2.2.1]heptane derivatives.

The present invention has been made in consideration of the above-mentioned point, and its object is to provide economical and efficient methods for producing bicyclo[2.2.1]heptane derivatives such as 2-methylene-3-methylbicyclo[2.2.1]heptane, 2,3-dimethylbicyclo[2.2.1]hept-2-ene, 2-ethylidenebicyclo[2.2.1]heptane and 2-ethylbicyclo[2.2.1]-hept-2-ene.

DISCLOSURE OF THE INVENTION

We, the present inventors have assiduously studied to attain the above-mentioned object and, as a result, have found that the object can be effectively attained by starting from relatively inexpensive and easily available compounds and selecting the reaction condition of the compounds. On the basis of this finding, we have completed the present invention.

Accordingly, the invention is summarized as follows:

<1> A method for producing bicyclo[2.2.1]heptane derivatives, which comprises reacting one or more $C_{3-4}$ acyclic olefins with cyclopentadiene to give bicyclo[2.2.1] heptene derivatives of the following general formula (I):

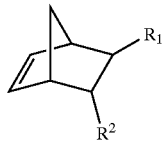

wherein $R^1$ and $R^2$ each represent a hydrogen atom, a methyl group or an ethyl group, and the sum of the carbon atoms in $R^1$ and $R^2$ is 1 or 2, followed by isomerizing them in the presence of an isomerization catalyst to give one or more bicyclo[2.2.1]heptane derivatives of the following general formula (II):

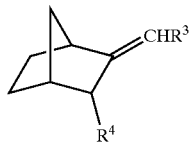

wherein $R^3$ and $R^4$ each represent a hydrogen atom or a methyl group, and the sum of the carbon atoms in $R^3$ and $R^4$ is 0 or 1, the following general formula (III):

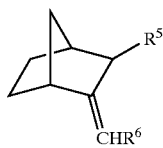

wherein $R^5$ and $R^6$ each represent a hydrogen atom or a methyl group, and the sum of the carbon atoms in $R^5$ and $R^6$ is 0 or 1, and the following general formula (IV):

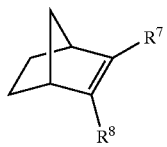

wherein $R^7$ and $R^8$ each represent a hydrogen atom, a methyl group or an ethyl group, and the sum of the carbon atoms in $R^7$ and $R^8$ is 1 or 2.

<2> The method for producing bicyclo[2.2.1]heptane derivatives of above <1>, wherein the acyclic olefin is 2-butene, the bicyclo[2.2.1]heptene derivative of general formula (I) is 5,6-dimethylbicyclo[2.2.1]hept-2-ene, the bicyclo[2.2.1]heptane derivative of formula (II) or (III) is 2-methylene-3-methylbicyclo[2.2.1]heptane, and the bicyclo[2.2.1]heptane derivative of formula (IV) is 2,3-dimethylbicyclo[2.2.1]hept-2-ene.

<3> The method for producing bicyclo[2.2.1]heptane derivatives of above <1>, wherein the acyclic olefin is 1-butene, the bicyclo[2.2.1]heptene derivative of formula (I) is 5-ethylbicyclo[2.2.1]hept-2-ene, the bicyclo[2.2.1] heptane derivative of formula (II) or (III) is 2-ethylidenebicyclo[2.2.1]heptane, and the bicyclo[2.2.1] heptane derivative of formula (IV) is 2-ethylbicyclo[2.2.1] hept-2-ene.

<4> A method for producing bicyclo[2.2.1]heptane derivatives, which comprises reacting one or more $C_{3-4}$ acyclic olefins with cyclopentadiene in the presence of an isomerization catalyst for simultaneous isomerization to give one or more bicyclo[2.2.1] heptane derivatives of the following general formula (II):

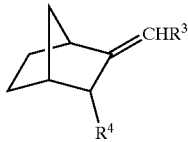

(II)

wherein $R^3$ and $R^4$ each represent a hydrogen atom or a methyl group, and the sum of the carbon atoms in $R^3$ and $R^4$ is 0 or 1, the following general formula (III):

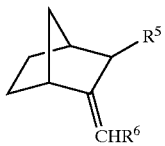

(III)

wherein $R^5$ and $R^6$ each represent a hydrogen atom or a methyl group, and the sum of the carbon atoms in $R^5$ and $R^6$ is 0 or 1, and the following general formula (IV):

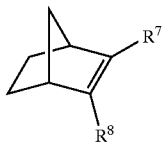

(IV)

wherein $R^7$ and $R^8$ each represent a hydrogen atom, a methyl group or an ethyl group, and the sum of the carbon atoms in $R^7$ and $R^8$ is 1 or 2.

<5> The method for producing bicyclo[2.2.1]heptane derivatives of above <4>, wherein the acyclic olefin is 2-butene, the bicyclo[2.2.1]heptane derivative of formula (II) or (III) is 2-methylene-3-methylbicyclo[2.2.1]heptane, and the bicyclo[2.2.1]heptane derivative of general formula (IV) is 2,3-dimethylbicyclo[2.2.1]hept-2-ene.

<6> The method for producing bicyclo[2.2.1]heptane derivatives of above <4>, wherein the acyclic olefin is 1-butene, the bicyclo[2.2.1]heptane derivative of formula (II) or (III) is 2-ethylidenebicyclo[2.2.1]heptane, and the bicyclo[2.2.1]heptane derivative of formula (IV) is 2-ethylbicyclo[2.2.1]hept-2-ene.

<7> A method for producing bicyclo[2.2.1]heptane derivatives, which comprises isomerizing bicyclo[2.2.1]heptene derivatives of the following general formula (I):

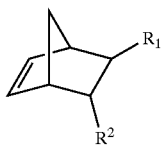

(I)

wherein $R^1$ and $R^2$ each represent a hydrogen atom, a methyl group or an ethyl group, and the sum of the carbon atoms in $R^1$ and $R^2$ is 1 or 2, in the presence of an isomerization catalyst to give one or more bicyclo[2.2.1]heptane derivatives of the following general formula (II):

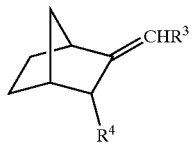

(II)

wherein $R^3$ and $R^4$ each represent a hydrogen atom or a methyl group, and the sum of the carbon atoms in $R^3$ and $R^4$ is 0 or 1, the following general formula (III):

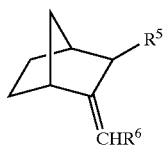

(III)

wherein $R^5$ and $R^6$ each represent a hydrogen atom or a methyl group, and the sum of the carbon atoms in $R^5$ and $R^6$ is 0 or 1, and the following general formula (IV):

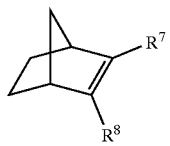

(IV)

wherein $R^7$ and $R^8$ each represent a hydrogen atom, a methyl group or an ethyl group, and the sum of the carbon atoms in $R^7$ and $R^8$ is 1 or 2.

<8> The method for producing bicyclo[2.2.1]heptane derivatives of above <7>, wherein the bicyclo[2.2.1]heptene derivative of formula (I) is 5,6-dimethylbicyclo[2.2.1]hept-2-ene, the bicyclo[2.2.1]heptane derivative of formula (II) or (III) is 2-methylene-3-methylbicyclo[2.2.1]heptane, and the bicyclo[2.2.1]heptane derivative of formula (IV) is 2,3-dimethylbicyclo[2.2.1]hept-2-ene.

<9> The method for producing bicyclo[2.2.1]heptane derivatives of above <7>, wherein the bicyclo[2.2.1]heptene derivative of formula (I) is 5-ethylbicyclo[2.2.1]hept-2-ene, the bicyclo[2.2.1]heptane derivative of formula (II) or (III) is 2-ethylidenebicyclo[2.2.1]heptane, and the bicyclo[2.2.1] heptane derivative of formula (IV) is 2-ethylbicyclo[2.2.1] hept-2-ene.

<10> The method for producing bicyclo[2.2.1]heptane derivatives of any of above <1> to <9>, wherein the isomerization catalyst is a solid acid catalyst.

<11> The method for producing bicyclo[2.2.1]heptane derivatives of any of above <1> to <6> and <10>, wherein dicyclopentadiene is used in place of cyclopentadiene and, while pyrolyzed into cyclopentadiene, it is reacted with one or more $C_{3-4}$ acyclic olefins.

BEST MODES OF CARRYING OUT THE INVENTION

Modes of carrying out the invention are described below.

According to the methods of the invention, $C_{3-4}$ acyclic olefins are reacted with cyclopentadiene to give the intended bicyclo[2.2.1]heptane derivatives. The $C_{3-4}$ acyclic olefins include, for example, 1-butene, 2-butene and propylene. Of those, 2-butene and 1-butene are preferred for the starting compounds in the invention.

One embodiment of the invention in which the acyclic olefin is 2-butene are described in detail.

In this embodiment, the starting compounds, 2-butene and cyclopentadiene are reacted with each other, and the resulting 5,6-dimethylbicyclo[2.2.1]hept-2-ene is isomerized in the presence of an isomerization catalyst to give 2-methylene-3-methylbicyclo[2.2.1]heptane and/or 2,3-dimethylbicyclo[2.2.1]hept-2-ene. The intermediate 5,6-dimethylbicyclo[2.2.1]hept-2-ene in this method of the invention is represented by the following chemical formula (V), and the final products 2-methylene-3-methylbicyclo[2.2.1]heptane and 2,3-dimethylbicyclo[2.2.1]hept-2-ene are by the following chemical formulae (VI) and (VII), respectively:

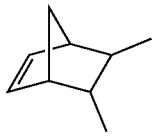

(V)

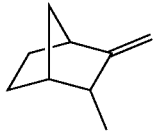

(VI)

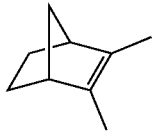

(VII)

According to the method, the bicyclo[2.2.1]heptane derivatives can be produced in at least 2 steps starting from inexpensive 2-butene and cyclopentadiene. In addition, they can be produced only in one step, as described hereinunder.

In the invention, the starting compounds, 2-butene and cyclopentadiene are reacted with each other. This is Diels-Alder reaction.

One starting compound, 2-butene may be trans-2-butene or cis-2-butene alone or may be their mixture. These are inexpensive and easily available.

The other stating compound, cyclopentadiene may be cyclopentadiene itself, or may also be derived from dicyclopentadiene in situ. When heated, dicyclopentadiene is readily pyrolyzed to give cyclopentadiene, and the resulting cyclopentadiene is substantially reacted with 2-butene. In other words, dicyclopentadiene is, while pyrolyzed to give cyclopentadiene, reacted with 2-butene through Diels-Alder reaction.

The blend ratio of the starting compounds, 2-butene and cyclopentadiene is not specifically defined. Preferably, however, 2-butene is excessive over its theoretical amount, or that is, the ratio of 2-butene/cyclopentadiene (by mol) is at least 1 or more. If the blend ratio of the starting compounds is smaller than 1, the reaction mixture may contain a large quantity of heavy compounds in addition to the intended products. More preferably, the blend ratio of the starting compounds falls between 2 and 20, even more preferably between 4 and 15.

In the invention, the starting compounds mentioned above are reacted with each other through Diels-Alder reaction. The reaction is generally effected at about 20 to 400° C., but preferably at 100 to 350° C. However, when dicyclopentadiene is used in place of cyclopentadiene and it is pyrolyzed into cyclopentadiene, the reaction is preferably effected at 150 to 350° C. This is for promoting the pyrolysis of dicyclopentadiene.

The Diels-Alder reaction pressure is not also specifically defined, and the reaction may be effected under any pressure. In general, the starting compounds are reacted under no specific pressure, but the vapor pressure of 2-butene increases the reaction pressure, and the pressure varies depending on the reaction temperature.

The Diels-Alder reaction gives the intermediate of the invention, 5,6-dimethylbicyclo[2.2.1]hept-2-ene of formula (V).

In the invention, this 5,6-dimethylbicyclo[2.2.1]hept-2-ene is isomerized in the presence of an isomerization catalyst.

Preferably, the isomerization catalyst is an acidic solid catalyst generally referred to as a solid acid catalyst. Concretely, for example, it includes metal oxides such as alumina, silica, titania, zirconia, chromia, zinc oxide, silica-alumina, silica-magnesia, alumina-boria, silica-boria, silica-zirconia; metal phosphates such as calcium phosphate, zirconium phosphate, calcium hydroxyapatite; metal sulfates such as magnesium sulfate, calcium sulfate, aluminium sulfate; phyllosilicates such as bentonite, montmorillonite, kaolin; clays such as activated clay, acid clay; solid acids prepared by infiltrating solid phosphoric acid or sulfuric acid into silica or alumina; and other ion-exchange resins and zeolite. Of those solid acid catalysts, silica-alumina, alumina-boria and zeolite have a high acid strength; titania and montmorillonite have a medium acid strength; and alumina and silica have a low acid strength.

The acid strength of catalyst is generally indicated by the acidity function thereof.

Of the solid acid catalysts mentioned above, preferred are those having a middle to high acid strength, as their ability to realize high conversion and high selectivity is good.

Correlated with the charge of the starting compounds into the reaction system, the catalyst is generally so controlled that its weight hourly space velocity, WHSV falls between 0.01 and 20 h$^{-1}$, preferably between 0.1 and 10 h$^{-1}$.

Like the Diels-Alder reaction, the isomerization may be effected in the absence or presence of a solvent such as an organic solvent.

The isomerization temperature preferably falls between about 20 and 400° C., more preferably between about 50 and 250° C. If the reaction temperature is lower than about 20° C., the isomerization will be delayed and the method will be impracticable; but if higher than 400° C., the products will be pyrolyzed. The preferred reaction temperature range varies, depending on the acid strength of the isomerization catalyst used. For example, when the acid strength of the isomerization catalyst used is high, the reaction temperature may fall between 20° C. and 150° C.; when it is medium, the temperature may fall between 150° C. and 250° C.; and when it is low, the temperature may fall between 250° C. and 400° C.

On the other hand, the isomerization pressure is not specifically defined, and may be effected under any pressure. In general, the isomerization is effected under no specific pressure.

In the manner as above, 2-methylene-3-methylbicyclo[2.2.1]heptane and/or 2,3-dimethylbicyclo[2.2.1]hept-2-ene of formulae (VI) and (VII) are obtained.

As mentioned above, the method of the invention comprises two steps of Diels-Alder reaction and isomerization to give the bicyclo[2.2.1]heptane derivatives of formulae (VI) and/or (VII). Apart from it, the bicyclo[2.2.1]heptane derivatives can also be produced in one step.

The method of the invention to give the bicyclo[2.2.1] heptane derivatives in one step comprises reacting 2-butene with cyclopentadiene in the presence of an isomerization catalyst for simultaneous isomerization to give 2-methylene-3-methylbicyclo[2.2.1]heptane and/or 2,3-dimethylbicyclo[2.2.1]hept-2-ene.

In this method, the two-step reactions go on efficiently and almost simultaneously.

The one-step method does not substantially differ from the two-step method except for the point that the isomerization catalyst is in the initial reaction system. Therefore, the details of the isomerization catalyst to be used and those of the starting compounds to be reacted and their blend ratio in the one-step method may be substantially the same as those in the above-mentioned two-step method. In addition, the two methods do not also substantially differ in point of the other reaction conditions such as reaction temperature and reaction pressure. Accordingly, the reaction temperature in the one-step method may fall between about 20 and 400° C., preferably between 100 and 350° C. More preferably, it falls between 150 and 350° C. when the reaction starts from dicyclopentadiene. Regarding the reaction pressure, the system does not require any specific pressure, and its pressure may be the vapor pressure at the reaction temperature.

According to the one-step method, 2-methylene-3-methylbicyclo[2.2.1]heptane and/or 2,3-dimethylbicyclo[2.2.1]hept-2-ene are also produced efficiently.

The above-mentioned methods apply to $C_{3-4}$ acyclic olefins except 2-butene to give the corresponding bicyclo[2.2.1]heptanes. For example, when 1-butene is used in place of 2-butene, it gives an intermediate, 5-ethylbicyclo[2.2.1]hept-2-ene, and then 2-ethylidenebicyclo[2.2.1]heptane and/or 2-ethylbicyclo[2.2.1]hept-2-ene through isomerization. When propylene is used in place of 2-butene, it gives an intermediate, 5-methylbicyclo[2.2.1]hept-2-ene, and then 2-methylidenebicyclo[2.2.1]heptane and/or 2-methylbicyclo[2.2.1]hept-2-ene through isomerization.

When a mixture of two or more $C_{3-4}$ acyclic olefins is used, it gives a mixture of intermediates, [2.2.1]heptene derivatives, and then a mixture of their isomers, [2.2.1] heptane derivatives through isomerization.

Therefore, for example, an acyclic olefin mixture of 2-butene and 1-butene gives a mixture of 2-methylene-3-methylbicyclo[2.2.1]heptane, 2,3-diemthylbicyclo[2.2.1]hept-2-ene, 2-ethylidenebicyclo[2.2.1]heptane and 2-ethylbicyclo[2.2.1]hept-2-ene.

The products of the above-mentioned methods, 2-methylene-3-methylbicyclo[2.2.1]heptane, 2,3-dimethylbicyclo[2.2.1]hept-2-ene, 2-ethylidenebicyclo[2.2.1]heptane and 2-ethylbicyclo[2.2.1]hept-2-ene are useful as synthetic materials for producing base oil to be in traction drive fluid.

The invention is described more concretely with reference to the following Examples, which, however, are not intended to restrict the scope of the invention.

EXAMPLE 1
(Two-Step Method)

324 g (5.78 mols) of mixed 2-butene (trans/cis=62/38), and 66.8 g (0.51 mols) of dicyclopentadiene were put into a one-liter stainless autoclave, and reacted at 240° C. for 3 hours. After cooled, the reaction mixture was distilled to collect 49 g of 140° C. fraction. The fraction was analyzed through mass spectrometry and nucleic magnetic resonance spectrometry, and the result confirmed that the fraction is 5,6-dimethylbicyclo[2.2.1]hept-2-ene.

A flow-type normal pressure reaction tube of quartz glass having an outer diameter of 20 mm and a length of 500 mm was filled with 25 g of alumina-boria (ShokubaiKasei Kogyo's C-15), and the fraction was introduced into it and isomerized at 155° C. and at a weight hourly space velocity (WHSV) of 1.0 $hr^{-1}$. This gave 48 g of an isomerized product of 5,6-dimethylbicyclo[2.2.1]hept-2—ene, containing 62% 2,3-dimethylbicyclo[2.2.1]hept-2-ene and 28% 2-methylene-3-methylbicyclo[2.2.1]heptane.

EXAMPLE 2
(Two-Step Method)

The same process as in Example 1 was repeated except for the following points. Trans-2-butene was used in place of the mixed 2-butene, a silica-alumina catalyst (Nikki Chemical's N-632L) was in place of the alumina-boria catalyst, and the isomerization was effected at 110° C. but not at 155° C. This gave 48 g of an isomerized product of 5,6-dimethylbicyclo[2.2.1]hept-2-ene, containing 52% 2,3-dimethylbicyclo[2.2.1]hept-2-ene and 20% 2-methylene-3-methylbicyclo[2.2.1]heptane.

EXAMPLE 3
(One-Step Method)

45 g (0.8 mols) of mixed 2-butene (trans/cis=62/38), 5.6 g (0.042 mols) of dicyclopentadiene, and 10 g of a catalyst, γ-alumina (Nikki Chemical's N613N) were put into a 200-cc stainless autoclave, and reacted at 240° C. for 5 hours. After cooled, this was analyzed through gas chromatography. The result confirmed that the reaction product contains 9% 2,3-dimethylbicyclo[2.2.1]hept-2-ene and 4% 2-methylene-3-methylbicyclo[2.2.1]heptane, in addition to 5,6-dimethylbicyclo[2.2.1]hept-2-ene.

EXAMPLE 4
(One-Step Method)

The same process as in Example 3 was repeated except that 15 g of silica-containing γ-alumina (Shokubai Kasei Kogyo's DHC-1) but not 10 g of γ-alumina was used as the catalyst. This gave 6 g of an isomerized product of 5,6-dimethylbicyclo[2.2.1]hept-2-ene, containing 64% 2,3-dimethylbicyclo[2.2.1]hept-2-ene and 26% 2-methylene-3-methylbicyclo[2.2.1]heptane.

EXAMPLE 5
(Two-Step Method)

The same process as in Example 1 was repeated except that 1-butene was used in place of the mixed 2-butene. This gave 93 g of an isomerized product of 5-ethylbicyclo[2.2.1]hept-2-ene, containing 67% 2-ethylbicyclo[2.2.1]hept-2-ene and 29% 2-ethylidenebicyclo[2.2.1]heptane.

EXAMPLE 6
(Two-Step Method)

80 g (1.43 mols) of mixed n-butene (35 wt. % 1-butene, 40 wt. % trans-2-butene, 25 wt. % cis-2-butene), and 13.2 g (0.10 mols) of dicyclopentadiene were put into a 200-cc stainless autoclave, and reacted at 240° C. for 3 hours. After cooled, the reaction mixture was distilled to collect 18 g of 140° C. fraction comprised of 75% 5-ethylbicyclo[2.2.1]hept-2-ene and 25% 5,6-dimethylbicyclo[2.2.1]hept-2-ene.

A flow-type normal pressure reaction tube of quartz glass having an outer diameter of 20 mm and a length of 500 mm was filled with 25 g of alumina-boria (ShokubaiKasei Kogyo's C-15), and the fraction was introduced into it and isomerized at 155° C. and at a weight hourly space velocity (WHSV) of 1.0 hr$^{-1}$. This gave 17 g of an isomerized product of 5,6-dimethylbicyclo[2.2.1]hept-2-ene and 5-ethylbicyclo[2.2.1]hept-2-ene, containing 15% 2,3-dimethylbicyclo[2.2.1]hept-2-ene, 6% 2-methylene-3-methylbicyclo[2.2.1]heptane, 49% 2-ethylbicyclo[2.2.2]hept-2-ene and 21% 2-ethylidenebicyclo[2.2.1]heptane.

Comparative Example 1

The same process as in Example 2 was repeated except that isomerizing the distilled fraction was tried with ceramic balls at 250° C., not with the silica-alumina catalyst (Nikki Chemical's N-632L) at 110° C., but in vain. In this, the starting compound 5,6-dimethylbicyclo[2.2.1]hept-2-ene was not isomerized and was directly collected still as it was after the process.

INDUSTRIAL APPLICABILITY

Starting from inexpensive acyclic olefins such as 2-butene and 1-butene, the methods of the invention give the intended bicyclo[2.2.1]heptane derivatives such as 2-methylene-3-methylbicyclo[2.2.1]heptane, 2,3-dimethylbicyclo[2.2.1] hept-2-ene, 2-ethylidenebicyclo[2.2.1]heptane and 2-ethylbicyclo[2.2.1]-hept-2-ene only in one step or two steps, and the methods are economical and efficient.

What is claimed is:

1. A method for producing bicyclo[2.2.1]heptane derivatives, which comprises reacting one or more C$_{3-4}$ acyclic olefins with cyclopentadiene to give bicyclo[2.2.1] heptene derivatives of the following general formula (I):

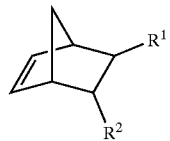

(I)

wherein R$^1$ and R$^2$ each represent a hydrogen atom, a methyl group or an ethyl group, and the sum of the carbon atoms in R$^1$ and R$^2$ is 1 or 2, followed by isomerizing them in the presence of an isomerization catalyst to give one or more bicyclo[2.2.1]heptane derivatives of the following general formula (II):

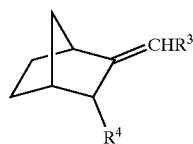

(II)

wherein R$^3$ and R$^4$ each represent a hydrogen atom or a methyl group, and the sum of the carbon atoms in R$^3$ and R$^4$ is 0 or 1, the following general formula (III):

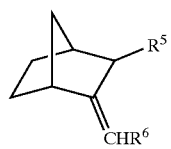

(III)

wherein R$^5$ and R$^6$ each represent a hydrogen atom or a methyl group, and the sum of the carbon atoms in R$^5$ and R$^6$ is 0 or 1, and the following general formula (IV):

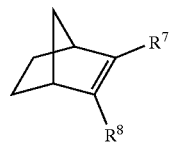

(IV)

wherein R$^7$ and R$^8$ each represent a hydrogen atom, a methyl group or an ethyl group, and the sum of the carbon atoms in R$^7$ and R$^8$ is 1 or 2.

2. The method for producing bicyclo[2.2.1]heptane derivatives as claimed in claim 1, wherein the acyclic olefin is 2-butene, the bicyclo[2.2.1]heptene derivative of formula (I) is 5,6-dimethylbicyclo[2.2.1]hept-2-ene, the bicyclo [2.2.1]heptane derivative of formula (II) or (III) is 2-methylene-3-methylbicyclo[2.2.1]heptane, and the bicyclo[2.2.1]heptane derivative of formula (IV) is 2,3-dimethylbicyclo[2.2.1]hept-2-ene.

3. The method for producing bicyclo[2.2.1]heptane derivatives as claimed in claim 1, wherein the acyclic olefin is 1-butene, the bicyclo[2.2.1]heptene derivative of formula (I) is 5-ethylbicyclo[2.2.1]hept-2-ene, the bicyclo[2.2.1] heptane derivative of formula (II) or (III) is 2-ethylidenebicyclo[2.2.1]heptane, and the bicyclo[2.2.1] heptane derivative of formula (IV) is 2-ethylbicyclo[2.2.1] hept-2-ene.

4. A method for producing bicyclo[2.2.1]heptane derivatives, which comprises reacting one or more C$_{3-4}$ acyclic olefins with cyclopentadiene in the presence of an isomerization catalyst for simultaneous isomerization to give one or more bicyclo[2.2.1]heptane derivatives of the following general formula (II):

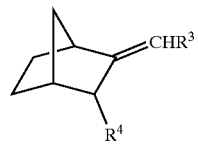

(II)

wherein R$^3$ and R$^4$ each represent a hydrogen atom or a methyl group, and the sum of the carbon atoms in R$^3$ and R$^4$ is 0 or 1, the following general formula (III):

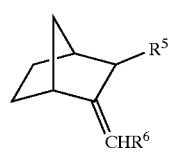

(III)

wherein R$^5$ and R$^6$ each represent a hydrogen atom or a methyl group, and the sum of the carbon atoms in R$^5$ and R$^6$ is 0 or 1, and the following general formula (IV):

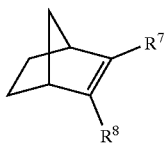

(IV)

wherein R⁷ and R⁸ each represent a hydrogen atom, a methyl group or an ethyl group, and the sum of the carbon atoms in R⁷ and R⁸ is 1 or 2.

5. The method for producing bicyclo[2.2.1]heptane derivatives as claimed in claim 4, wherein the acyclic olefin is 2-butene, the bicyclo[2.2.1]heptane derivative of formula (II) or (III) is 2-methylene-3-methylbicyclo[2.2.1]heptane, and the bicyclo[2.2.1]heptane derivative of formula (IV) is 2,3-dimethylbicyclo[2.2.1]hept-2-ene.

6. The method for producing bicyclo[2.2.1]heptane derivatives as claimed in claim 4, wherein the acyclic olefin is 1-butene, the bicyclo[2.2.1]heptane derivative of formula (II) or (III) is 2-ethylidenebicyclo[2.2.1]heptane, and the bicyclo[2.2.1]heptane derivative of formula (IV) is 2-ethylbicyclo[2.2.1]hept-2-ene.

7. A method for producing bicyclo[2.2.1]heptane derivatives, which comprises isomerizing bicyclo[2.2.1] heptene derivatives of the following general formula (I):

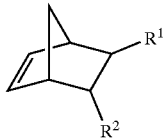

(I)

wherein R¹ and R² each represent a hydrogen atom, a methyl group or an ethyl group, and the sum of the carbon atoms in R¹ and R² is 1 or 2, in the presence of an isomerization catalyst to give one or more bicyclo[2.2.1]heptane derivatives of the following general formula (II):

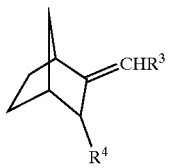

(II)

wherein R³ and R⁴ each represent a hydrogen atom or a methyl group, and the sum of the carbon atoms in R³ and R⁴ is 0 or 1, the following general formula (III):

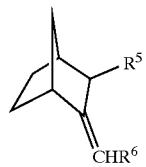

(III)

wherein R⁵ and R⁶ each represent a hydrogen atom or a methyl group, and the sum of the carbon atoms in R⁵ and R⁶ is 0 or 1, and the following general formula (IV):

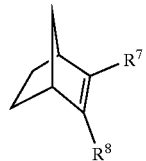

(IV)

wherein R⁷ and R⁸ each represent a hydrogen atom, a methyl group or an ethyl group, and the sum of the carbon atoms in R⁷ and R⁸ is 1 or 2.

8. The method for producing bicyclo[2.2.1]heptane derivatives as claimed in claim 7, wherein the bicyclo[2.2.1] heptene derivative of formula (I) is 5,6-dimethylbicyclo [2.2.1]hept-2-ene, the bicyclo[2.2.1]heptane derivative of formula (II) or (III) is 2-methylene-3-methylbicyclo[2.2.1] heptane, and the bicyclo[2.2.1]heptane derivative of formula (IV) is 2,3-dimethylbicyclo[2.2.1]hept-2-ene.

9. The method for producing bicyclo[2.2.1]heptane derivatives as claimed in claim 7, wherein the bicyclo[2.2.1] heptene derivative of formula (I) is 5-ethylbicyclo[2.2.1] hept-2-ene, the bicyclo[2.2.1]heptane derivative of formula (II) or (III) is 2-ethylidenebicyclo[2.2.1]heptane, and the bicyclo[2.2.1]heptane derivative of formula (IV) is 2-ethylbicyclo[2.2.1]hept-2-ene.

10. The method for producing bicyclo[2.2.1]heptane derivatives as claimed in claim 1, wherein the isomerization catalyst is a solid acid catalyst.

11. The method for producing bicyclo[2.2.1]heptane derivatives as claimed in claim 1, wherein dicyclopentadiene is used in place of cyclopentadiene and, while pyrolyzed into cyclopentadiene, it is reacted with one or more $C_{3-4}$ acyclic olefins.

12. The method for producing bicyclo[2.2.1]heptane derivatives as claimed in claim 7, wherein the isomerization catalyst is a solid acid catalyst.

13. The method for producing bicyclo[2.2.1]heptane derivatives as claimed in claim 10, wherein dicyclopentadiene is used in place of cyclopentadiene and, while pyrolyzed into cyclopentadiene, it is reacted with one or more $C_{3-4}$ acyclic olefins.

* * * * *